(12) United States Patent
Yao

(10) Patent No.: US 10,482,556 B2
(45) Date of Patent: Nov. 19, 2019

(54) METHOD OF DELIVERING DECISION SUPPORT SYSTEMS (DSS) AND ELECTRONIC HEALTH RECORDS (EHR) FOR REPRODUCTIVE CARE, PRE-CONCEPTIVE CARE, FERTILITY TREATMENTS, AND OTHER HEALTH CONDITIONS

(75) Inventor: Mylene Yao, Los Altos, CA (US)

(73) Assignee: UNIVFY Inc., Los Altos, CA (US)

(*) Notice: Subject to any disclaimer, the term of this patent is extended or adjusted under 35 U.S.C. 154(b) by 970 days.

(21) Appl. No.: 13/160,245

(22) Filed: Jun. 14, 2011

(65) Prior Publication Data

US 2011/0313790 A1    Dec. 22, 2011

Related U.S. Application Data

(60) Provisional application No. 61/356,646, filed on Jun. 20, 2010.

(51) Int. Cl.
| | | |
|---|---|---|
| G16H 50/50 | (2018.01) | |
| G16H 50/20 | (2018.01) | |
| G16H 10/60 | (2018.01) | |
| G06Q 50/24 | (2012.01) | |
| G06Q 50/22 | (2018.01) | |
| G06F 19/00 | (2018.01) | |

(52) U.S. Cl.
CPC .......... *G06Q 50/24* (2013.01); *G06F 19/00* (2013.01); *G06Q 50/22* (2013.01); *G16H 50/20* (2018.01); *G16H 50/50* (2018.01); *G16H 10/60* (2018.01)

(58) Field of Classification Search
CPC .... G06Q 50/22–24; G06F 19/322–327; G16H 50/20
USPC .......................................................... 705/2–3
See application file for complete search history.

(56) References Cited

U.S. PATENT DOCUMENTS

| | | |
|---|---|---|
| 4,816,257 A | 3/1989 | Buster et al. |
| 5,612,869 A | 3/1997 | Letz et al. |
| 5,619,991 A | 4/1997 | Sloane |
| (Continued) | | |

FOREIGN PATENT DOCUMENTS

| | | |
|---|---|---|
| WO | 2010/045463 A2 | 4/2010 |
| WO | 2010045463 A2 | 4/2010 |

OTHER PUBLICATIONS

International Search Report dated Feb. 3, 2012, for counterpart application No. PCT/US11/40384, (inventor Mylene Yao; filed on Jun. 14, 2011).

(Continued)

*Primary Examiner* — Sheetal R Paulson
(74) *Attorney, Agent, or Firm* — Karen Canaan; CanaanLaw, P.C.

(57) ABSTRACT

Provided are methods of delivering decision support systems (DSSs) to healthcare providers, patients, and/or consumers with or without integrated electronic health records (EHRs) for reproductive care and other health conditions. The DSS platforms of the present invention include predication models based upon de-identified data sets and customized algorithms that may be clinic specific, region specific, and/or population specific. The DSS platforms of the present invention also include methods of providing third party payments of an individual's medical bills, wherein the third party is not capable of viewing the personal health identifiers of the individual.

35 Claims, 1 Drawing Sheet

(56) References Cited

U.S. PATENT DOCUMENTS

| | | | |
|---|---|---|---|
| 5,809,997 A | 7/1998 | Wolf | |
| 5,812,984 A | 7/1998 | Goltra | |
| 5,816,246 A | 10/1998 | Mirza | |
| 5,832,450 A | 11/1998 | Myers et al. | |
| 5,924,074 A | 7/1999 | Evans | |
| 6,278,999 B1 | 8/2001 | Knapp | |
| 6,347,329 B1 | 2/2002 | Evans | |
| 6,523,009 B1 | 2/2003 | Wilkins | |
| 6,529,876 B1 | 3/2003 | Dart et al. | |
| 6,597,946 B2 | 7/2003 | Avrahami et al. | |
| 6,600,696 B1 | 7/2003 | Lynn | |
| 7,076,437 B1 | 7/2006 | Levy | |
| 7,188,073 B1 | 3/2007 | Tam et al. | |
| 7,188,082 B2 | 3/2007 | Keane et al. | |
| 7,263,493 B1 | 8/2007 | Provost | |
| 7,275,220 B2 | 9/2007 | Brummel et al. | |
| 7,295,988 B1 | 11/2007 | Reeves | |
| 7,311,666 B2 | 12/2007 | Stupp et al. | |
| 7,361,142 B2 | 4/2008 | Suda | |
| 7,392,199 B2 | 6/2008 | Karlov et al. | |
| 7,438,228 B2 | 10/2008 | Robertson et al. | |
| 7,461,079 B2 | 12/2008 | Walker et al. | |
| 7,487,102 B2 | 2/2009 | Castille | |
| 7,643,969 B2 | 1/2010 | Soto et al. | |
| 7,685,000 B1 | 3/2010 | Petit | |
| 7,703,042 B2 | 4/2010 | Brummel et al. | |
| 7,730,024 B2 | 6/2010 | Harinth | |
| 7,853,456 B2 | 12/2010 | Soto et al. | |
| 8,160,977 B2 | 4/2012 | Poulin | |
| 2002/0016529 A1* | 2/2002 | Iliff | G06Q 50/22 600/300 |
| 2003/0017481 A1 | 1/2003 | Golub et al. | |
| 2003/0105731 A1 | 6/2003 | Lapointe | |
| 2004/0193019 A1 | 9/2004 | Wei | |
| 2005/0202426 A1 | 9/2005 | Short et al. | |
| 2005/0203773 A1* | 9/2005 | Soto | G06Q 40/08 705/2 |
| 2006/0052945 A1* | 3/2006 | Rabinowitz | G06F 19/24 702/20 |
| 2006/0173663 A1 | 3/2006 | Langheier et al. | |
| 2006/0147900 A1 | 7/2006 | Zhang | |
| 2007/0027636 A1 | 2/2007 | Rabinowitz et al. | |
| 2007/0053563 A1 | 3/2007 | Tu et al. | |
| 2007/0055552 A1 | 3/2007 | St. Clair et al. | |
| 2007/0082329 A1* | 4/2007 | Williams et al. | 435/4 |
| 2007/0130206 A1 | 6/2007 | Zhou et al. | |
| 2007/0162992 A1 | 7/2007 | Burns | |
| 2007/0178501 A1 | 8/2007 | Rabinowitz et al. | |
| 2007/0192134 A1 | 8/2007 | Littenberg et al. | |
| 2007/0192137 A1* | 8/2007 | Ombrellaro | G06Q 10/10 705/2 |
| 2007/0238111 A1 | 10/2007 | Cibelli et al. | |
| 2008/0133275 A1 | 6/2008 | Haug et al. | |
| 2008/0162992 A1 | 7/2008 | Moser et al. | |
| 2008/0163824 A1 | 7/2008 | Moser et al. | |
| 2009/0029375 A1 | 1/2009 | Jupe et al. | |
| 2009/0259491 A1 | 10/2009 | Busch | |
| 2010/0036192 A1 | 2/2010 | Yao et al. | |
| 2010/0049689 A1 | 2/2010 | Jorg et al. | |
| 2010/0112605 A1 | 5/2010 | Paul et al. | |
| 2010/0138199 A1 | 6/2010 | Soto et al. | |
| 2011/0078329 A1 | 3/2011 | Steiner | |
| 2011/0099027 A1* | 4/2011 | Weathers | G06F 19/328 705/2 |
| 2011/0173018 A1 | 7/2011 | Hoffner et al. | |
| 2011/0288780 A1* | 11/2011 | Rabinowitz et al. | 702/19 |

OTHER PUBLICATIONS

American Society for Reproductive Medicine (ASRM), Guidelines on Number of Embryos Transferred, Fertility and Sterility 90:S163-S164 (2008).

Banerjee et al., Deep Phenotyping to Predict Live Birth Outcomes in In Vitro Fertilization, PNAS 107 (31):13570-13575 (2010).

Bonduelle et al., A Multi-Centre Cohort Study of the Physical Health of 5-Year-Old Children Conceived After Intracytoplasmic Sperm Injection, In Vitro Fertilization and Natural Conception, Human Reproduction 20(2):413-419 (2005).

Friedman, Greedy Function Approximation: A Gradient Boosting Machine, IMS 1999 Reitz Lecture, Feb. 24, 1999 (modified Mar. 15, 2000 and Apr. 15, 2001).

Friedman, Stochastic Gradient Boosting, Stanford University Technical Paper, Mar. 26, 1999.

Friedman, Tutorial: Getting Started in MART with R, Stanford University Technical Paper, May 13, 2002.

Friedman et al., Multiple Additive Regression Trees with Application in Epidemiology, Statistics in Medicine 22:1365-1381 (2003).

Horvitz, From Data to Predictions and Decisions: Enabling Evidence-Based Healthcare, Computing Community Consortium, Version 6: Sep. 16, 2010.

Hseih et al., Decreased Expression of Mitochondrial Genes in Human Unfertilized Oocytes and Arrested Embryos, Fertility and Sterility 81 Supp. 1, pp. 912-918, Mar. 2004.

Jun et al., Defining Human Embryo Phenotypes by Cohort-Specific Prognostic Factors, PLoS One 3(7):e2562, pp. 1-7 (2008).

Kalu et al., Reducing Multiple Pregnancy in Assisted Reproduction Technology: Towards a Policy of Single Blastocyst Transfer in Younger Women, British Journal of Obstetrics and Gynecology (BJOG) 115:1143-1150 (2008).

Khalaf et al., Selective Single Blastocyst Transfer Reduces the Multiple Pregnancy Rate and Increases Pregnancy Rates: A Pre- and Postintervention Study, British Journal of Obstetrics and Gynecology (BJOG) 115:385-390 (2008).

Li et al., Analysis of Gene Expression in Single Human Oocytes and Preimplantation Embryos, Biochem. and Biophys. Res. Comm. 340(1):48-53 (2006).

Martin et al., Births: Final Data for 2006, National Vital Statistics Reports (NVSR) 57(7):1-102 (2009).

Osterman et al., Expanded Health Data From the New Birth Certificate, 2006, National Vital Statistics Reports (NVSR) 58(5):1-24 (2009).

Passmore et al., Assessing Decision Tree Models for Clinical In-Vitro Fertilization Data, Technical Report TR03-296, Department of Computer Science and Statistics, University of Rhode Island, Mar. 2004.

Pinborg et al., Neonatal Outcome in a Danish National Cohort of 8602 Children Born After in Vitro Fertilization or Intracytoplasmic Sperm Injection: The Role of Twin Pregnancy, Acta Obstet Gynecol Scand 83: 1071-1078 (2004).

Styer et al., Single-Blastocyst Transfer Decreases Twin Gestation Without Affecting Pregnancy Outcome, Fertility and Sterility 89(6):1702-1708 (2008).

Sunderam et al., Assisted Reproductive Technology Surveillance—United States, 2006, Morbidity and Mortality Weekly Report (MMWR) 58(SS05):1-25 (2009).

Sutcliffe et al., Outcome of Assisted Reproduction (Review), Lancet 370:351-59 (2007).

Van Voorhis, In Vitro Fertilization, The New England Journal of Medicine 356:379-86 (2007).

Minaretzis et al., Multivariate Analysis of Factors Predictive of Successful Live Births in in Vitro Fertilization (IVF) Suggests Strategies to Improve IVF Outcome, Journal of Assisted Reproduction and Genetics 15(6):365-371 (1998).

Weed and Hertzberg, The Use and Construction of Problem-Knowledge Couplers, the Knowledge Coupler Editor, Knowledge Networks, and the Problem-Oriented Medical Record for the Microcomputer, IEEE:831-836 (1983).

European Extended Search Report dated Jan. 18, 2017, for the counterpart case EP11798645.5.

Iskander et al., Automatic Pupillometry From Digital Images, IEEE Transactions on Biomedical Engineering 51 (9):1619-1627 (2004).

Edgerton et al., Data Mining for Gene Networks Relevant to Poor Prognosis in Lung Cancer Via Backward-Chaining Rule Induction, Cancer Informatics 3:93-114 (2007).

Chan et al., Discovering approximate-associated sequence patterns for protein-DNA interactions, Bioinformatics 27 (4):471-478 (2011).

(56) References Cited

OTHER PUBLICATIONS

Kuzdsal et al., Biomarker Discovery and Analysis Platform: Application to Alzheimer's Disease, Biotechniques 39 (4):606-607 (2005).
Kulasingam et al., Tissue culture-based breast cancer biomarker discovery platform, Int. J. Cancer 123:2007-2012 (2008).
Eschrich et al., Systems Biology Modeling of the Radiation Sensitivity Network: A Biomarker Discovery Platform, Int. J. Oncol. Biol. Phys. 75(2):497-505 (2009).
Zheng and Agresti, Summarizing the predictive power of a generalized linear model, Statistics in Medicine 19:1771-1781 (2000).
Steyerberg et al., Assessing the performance of prediction models: a framework for some traditional and novel measures, Epidemiology 21(1):128-138.

* cited by examiner

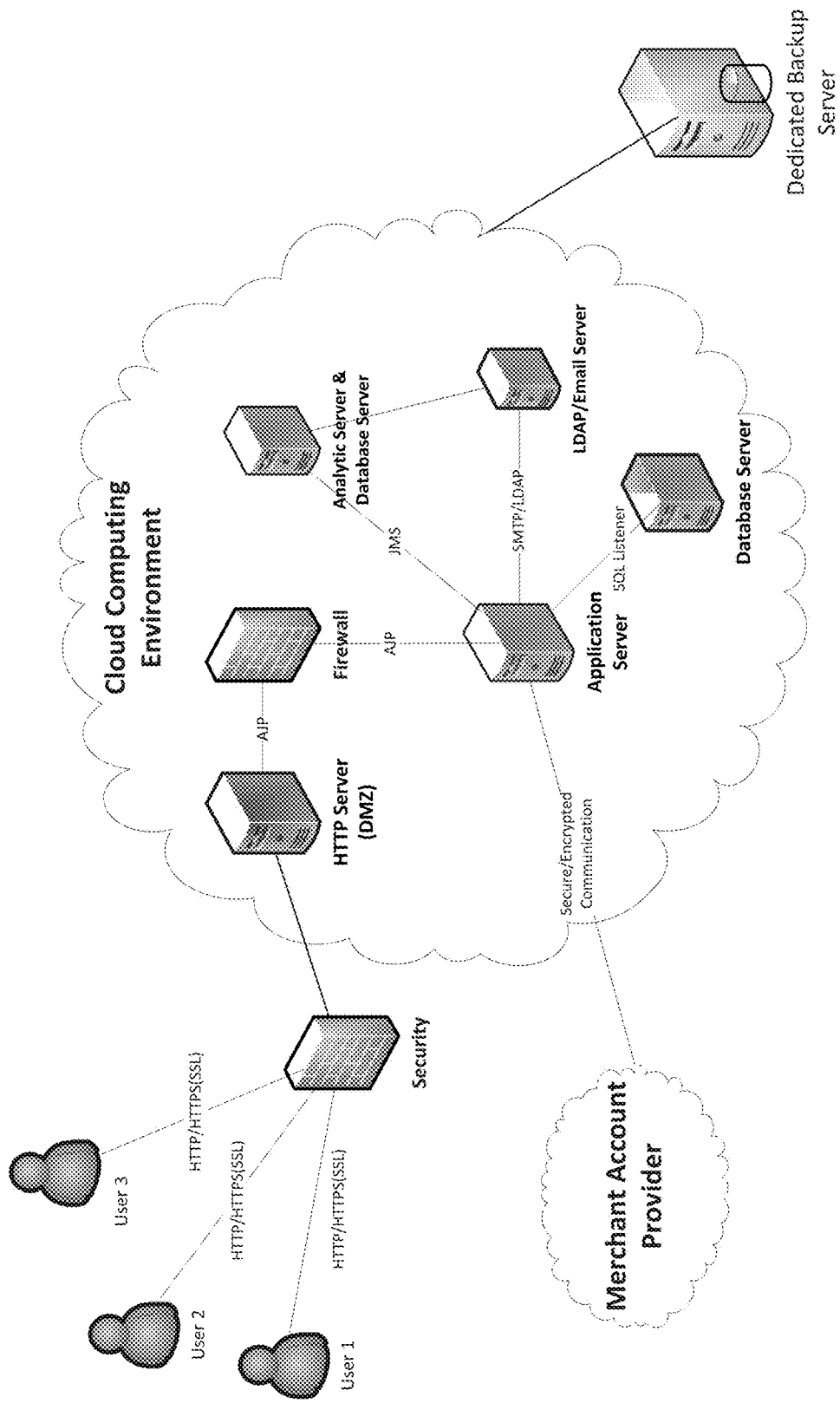

METHOD OF DELIVERING DECISION SUPPORT SYSTEMS (DSS) AND ELECTRONIC HEALTH RECORDS (EHR) FOR REPRODUCTIVE CARE, PRE-CONCEPTIVE CARE, FERTILITY TREATMENTS, AND OTHER HEALTH CONDITIONS

CROSS-REFERENCE TO RELATED APPLICATIONS

This application claims the benefit under 35 U.S.C. § 119(e) of U.S. Provisional Patent Application No. 61/356,646, filed on Jun. 20, 2010, which is incorporated in its entirety herein.

TECHNICAL FIELD

The present invention relates generally to the delivery of decision support systems (DSSs) and electronic health records (EHRs). More specifically, the present invention relates to methods of delivering DSSs to healthcare providers, patients, and/or consumers with or without integrated EHRs, for reproductive care and other health conditions.

BACKGROUND OF THE INVENTION

DSSs are currently used for medical purposes as well as consumer-facing online and mobile products. Within the context of medical use, DSSs include the following: (i) expensive, stand-alone products that contain sensory components that directly measure physiological inputs; (ii) integrated components in hospital-outfitted or network-outfitted electronic medical records (EMRs); (iii) inexpensive calculators designed for healthcare professionals (e.g., EPOCRATES®, Epocrates, Inc., San Mateo, Calif.); and (iv) free calculators that populate many healthcare-related content websites to engage viewers (e.g., WEBMD®, WebMD, LLC, New York, N.Y.).

Often, the core function of a DSS is one or more algorithms, which, when executed, provides the probability of a certain clinical or health outcome. Such probabilities are useful tools for healthcare providers in making health-related decisions relating to patient treatment and also to consumers in taking steps to implement and/or maintain a healthy lifestyle. Most patients and consumers, and even many healthcare providers, may not be aware of, or have the time to scrutinize, the quality of these decision support tools. For those healthcare providers who devote the time and expense to research and implement high quality calculators and decision tools, their improved quality of counseling and healthcare delivery may not be acknowledged and/or recognized on the clinical side by their healthcare organizations, patients, payors, and healthplan sponsors. Such shortcomings are not conducive to the widespread implementation and use of rigorously validated DSSs.

Currently, EHR platforms are designed to create and maintain health records pertaining to the following: (i) a patient's general medical health; (ii) a patient's engagement with their healthcare provider; (iii) improved physician-patient-family communications; and (iv) a reduction in the redundancy and incidence of errors in a patient's health care records. These EHR platforms, while useful, do not cater to the special needs of individuals who have health-lifestyle-medical needs that require creating and keeping records that are not supported by standard EHR platforms. Further, the style and language that currently available EHRs use to prompt input from individuals is not designed to optimize extraction of accurate and essential data from complex medical history, specialized medical needs, or medical history that is closely intertwined with lifestyle factors, such as reproductive and developmental history, peri-conceptional concerns, fertility data, and/or chronic illnesses.

EHR platforms are also not designed to verify or require certain personal health data input that is required to run prediction models. To the best of the inventor's knowledge, there are no known EHRs that are integrated with validated prediction models, transparency of data source, and/or methodology that allow the quality of the EHRs to be objectively assessed. In this regard, while an individual may be diligent in creating and maintaining their own personal health records, the individual receives no prognostic benefit from the data input exercise. Further, because currently available predication models are not validated, the individual has no foundation for verifying the accuracy of the prediction.

Within the context of reproductive care, current EHR systems are not being used to support personal health data input that is required to make predictions that address probable outcomes of specific treatments, such as for example, the prognosis of a live birth event in fertility treatments or the prognosis of the outcome of a particular disease state. In a similar vein, no currently available DSS method is being used to provide personalized prognostic information relating to patient fertility treatments.

While DSSs and EHRs are currently used for medical and consumer products as described above, to the best of the inventor's knowledge, these two systems have not been effectively used in concert to deliver tools for use by health care professionals and/or consumers.

SUMMARY OF THE INVENTION

The present invention provides an EHR-driven DSS that overcomes the shortcomings and challenges in the art.

In one embodiment of the invention, there is provided a method comprising the steps of: (a) establishing an electronic decision support system (DSS) comprising a prediction model for a health condition or disease state; (b) delivering the DSS to an individual or healthcare provider, wherein the prediction model is developed and validated based upon clinic-specific, region-specific, and/or population-specific variables. The clinic-specific, region-specific, and/or population-specific variables may be selected from the group consisting of demographic variables, clinical variables, laboratory variables, or combinations thereof. Demographic variables may be selected from the group consisting of ethnicity, household income level, and education. Laboratory variables may be selected from the group consisting of test results of body fluids, tissue level data, imaging results, and biomarker test results. Tissue level data may be selected from the group consisting of immunoassays, quantitative PCR (qPCR), semi-quantitative measurement of transcriptome by gene expression arrays, or whole-transcriptome sequencing. Biomarker test results may be selected from the group consisting of genetic marker tests results and genetic data extracted from discovery platforms.

In another embodiment of the invention, the prediction model is selected from the group consisting of machine learning, logistic regression, linear regression, and combinations of any of the foregoing. The machine learning may comprise a boosted tree approach.

In a further embodiment of the invention, the prediction model is validated against a set of quantitative and statistical criteria. The quantitative and statistical criteria may be selected from the group consisting of posterior probability of an event, area under the curve, calibration, and reclassification.

In another embodiment of the invention, the prediction model is a Diversity Prediction Model that includes a Diversity set selected from the group consisting of aggregate de-identified phenotypic data sets from clinics, phenotypic data sets with personal health identifiers from individuals, and a combination of aggregate and individual data sets. Phenotypic profiling for an individual may be carried out in real-time against a library of known profiles.

In a further embodiment of the invention, a clinic may be compensated by a company that is using the de-identified data sets for the development of the Diversity Prediction Model. The clinic may b compensated by the company based upon a number of factors, including without limitation, the relative size of the de-identified data set as a portion of the Diversity Set; the clinic's contribution to the establishment of phenotypic profiles obtained from the de-identified data sets; and the clinic's contribution to quantitative measures of the performance of the model. Quantitative measures may include without limitation, predictive power, discrimination, calibration, and reclassification.

In another embodiment of the invention, the DSS is implemented in a business-to-business architecture, wherein the DSS is developed by a company and provided to a clinic without interaction by an individual; a business-to-business-to-consumer architecture, wherein the DSS is developed by a company and provided to a clinic with interaction by an individual; or a business-to-consumer architecture, wherein the DSS is developed by a company and provided directly to an individual.

In a further embodiment of the invention, the DSS may be a stand-alone DSS or it may be integrated with an electronic health record (EHR). The EHR may comprise an internet platform that supports entry of personal health data of an individual, wherein the personal health data may be entered into the EHR platform by the individual, a physician, a healthcare provider, or a clinic administrator, each of which may individually designate sharing privileges for the EHR, wherein the sharing privileges may be tailored to specify time limits for sharing. In addition, the EHR platform may comprise support of clinic oriented services and direct to consumer goods and services.

In another embodiment of the invention, the DSS provides personalized predictions based upon the information entered into the EHR for a specific condition or disease state. Where the EHR is specific for fertility treatments, the DSS provides personalized predictions of at least one fertility outcome for the individual. In one embodiment of the invention, the fertility outcome is the probability of a live birth event. Where the EHR is specific for menstrual and/or hormonal abnormalities and the DSS provides personalized predictions of possible conditions causing the menstrual and/or hormonal abnormalities in the individual. The EHR may also be specific for a variety of disease states, wherein the DSS provides personalized predictions regarding treatment of the disease state for the individual. Disease states may include without limitation, cancer, glaucoma, diabetes, heart disease, rheumatoid arthritis, and multiple sclerosis.

In a further embodiment of the invention, the EHR platform further comprises additional platforms selected from the group consisting of consultation platforms, consumer services platforms, and consumer goods platforms. In one embodiment, the consultation platforms may comprise features selected from the group consisting of physician biographies, physician schedules, physician consultation request modules, and payment modules.

In another embodiment of the invention, there is provided a method comprising the steps of: (a) obtaining a medical bill directed to an individual for which a third party is responsible for payment of the medical bill; (b) entering the medical bill into an electronic health record (EHR) platform (EHR) and identifying the payor of the medical bill to be a third party; and (c) obtaining a promotional code for payment of the medical bill from the third party and entering said promotional code into the EHR, wherein the promotional code initiates payment of the medical bill by the third party, wherein the third party has no ability to access to any personal health information of the individual by way of the promotional code payment process. Third party may be an entity selected from an employer and an insurance company.

In a further embodiment of the invention, there is provided a system comprising: (a) an electronic health care (EHR) platform by way of an internet connection, wherein a user enters information into the EHR platform; (b) an application server (AP) that communicates with the computer terminal, wherein the AP comprises customized algorithms, wherein the algorithms are used to interpret the information entered into the EHR platform and provide a prediction model for a health condition or disease state; and (c) a database server (DP) that communicates with the AP, wherein the DB stores the information entered on the EHR platform and provides encryption to keep the information secure. A user of the system may be selected from the group consisting of an individual, a physician, a healthcare provider, and a clinic administrator. In one embodiment, the EHR platform is provided in an application selected from the group consisting of an electronic application on a local computer, an online web application, a mobile application, and a web-based application designed for mobile devices. Electronic applications may be located on a personal computer or a clinic server. In one embodiment, the customized algorithm is comprised of de-identified data from a single clinic. In another embodiment, the customized algorithm is comprised of de-identified data from more than one clinic. In a further embodiment, the customized algorithm provides a prediction model for a condition or disease state based upon the information provided by the user in the EHR.

Additional advantages and embodiments of the invention will be provided, without limitation, in the detailed description of the invention that is set forth below.

BRIEF DESCRIPTION OF THE DRAWINGS

FIG. 1 is a schematic of a computing architecture for the EHR-drive DSS of the present invention.

DETAILED DESCRIPTION OF THE INVENTION

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The terms "comprises" and/or "comprising," as used in this specification and the appended claims, specify the presence of stated features, integers, steps, operations, elements, and/or components, but do not preclude the presence or addition of one or more other features, integers, steps, operations, elements, components, and/or groups thereof.

As used herein, the term "individual" is meant to refer to a human person that may be a "patient" undergoing medical treatment for a particular condition or disease or a "consumer" that is not undergoing medical treatment for any particular condition or disease. The term "patient" as used herein refers to an individual that is under the care of a physician or a clinic. Within the context of fertility treatments, the term "patient" refers to a female or male human being undergoing fertility diagnoses, analyses, and/or treatments under the care of a physician or a clinic.

As used herein, the term "algorithm" means a set of logic and/or mathematical relationships that govern a set of independent variables.

As used herein, the term "decision support system" or "DSS" means a medical, health, or lifestyle-related prediction tool that takes in a person's health data and provides an output to inform the probability of having a certain health condition.

As used herein, the term "electronic health record" or "EHR" is used to refer to both electronic personal health records or (EPHR) and electronic medical records (EMR). Within the context of the present invention, the term "EPHR" refers to health information that is inputted into an appropriate electronic database by an individual or the individual's healthcare provider in response to a questionnaire. As used herein, the term "EMR" refers to medical records that are generated by a healthcare provider, clinic, hospital, and/or laboratory and inputted into an appropriate electronic database by a healthcare provider or a clinic, hospital, and/or laboratory affiliated. In this regard, it is to be understood that the term "EHR" as used herein includes both EPHRs provided by the individual and EMRs provided by a healthcare provider, clinic, hospital, and/or laboratory.

As used herein, the terms "clinic" refers organizations that provide health care and includes without limitation, stand-alone outpatient units, a network of outpatient units dispersed regionally or nationally, mobile health units, and facilities that provide inpatient care such as hospitals, hospices, and/or rehabilitation centers.

As used herein, the term "de-identified data set" refers to data on an individual that has been stripped of any identifying information regarding the individual. The de-identified data may be obtained from one clinic or from different clinics. It will be understood by those of skill in the art that within the context of the present invention, the de-identified data sets will be in compliance with HIPAA, HITECH, and privacy and consumer laws.

DSS Development and Delivery

The present invention includes methods of developing and delivering a DSS to healthcare providers and individuals. The DSS of the present invention may be a stand-alone DSS or a DSS integrated with an EHR (i.e., an EHR-driven DSS). An advantage of the DSS methods of the present invention is that they allow for the development and validation of clinic-specific, region-specific, and/or population-specific prediction models by using non-overlapping training and test sets that pertain to the same patient population. Where the DSS is a stand-alone DSS, it is to be understood that the DSS may receive data from a source selected from the group consisting of EPHRs, EMRs, clinical laboratories, voice input, text searches, images, and devices that receive sensory input of physiologic or medical relevance and translate the sensory input into electronic and quantitative format.

Within the context of the present invention, training and test sets comprise variables selected from the group consisting of demographic variables (e.g., ethnicity, household income level, education), clinical data (e.g., symptoms, findings on physical examination), and laboratory data. Laboratory data includes without limitation, lab test results pertaining to any bodily fluids, tissue-level data, imaging results, and biomarker test results, which may or may not include genetic markers or genetic data extracted from discovery platforms. Examples of tissue-level data includes without limitations, immunoassays, quantitative PCR (qPCR), semi-quantitative measurement of transcriptome by gene expression arrays, or whole-transcriptome sequencing.

Each prediction model of the present invention has clearly defined inclusion and exclusion criteria, limitations, and provides probability of the queried clinical or health outcome, along with a computed estimation of error range. Statistical methods used to generate the prediction model may be, for example, via machine learning, such as boosted tree, or a blended approach that combines machine learning, logistic regression or linear regression, and other mathematical relationships. Each prediction model is validated according to a set of quantitative and statistical criteria, including but not limited to posterior probability of an event (e.g., expressed in posterior log of odds ratio between customized model-predicted and control model-predicted probabilities), area under the curve in a receiver-operating curve analysis to determine the ability of the prediction model to discriminate among different actual probabilities, calibration, reclassification (also known as utility of the prediction model). As is understood by those of skill in the art, the validation parameters of the prediction models of the present invention are compared to those of a control model with specific criteria.

The steps required to generate and validate prediction models, may or may not be automated. Where the generation and validation of the prediction model is not automated, the combined expertise of a statistician, physician and scientist may be required in order to manually annotate the variable naming conventions of each clinic included in the DSS and also to scrutinize the process for unexpected nuances of each clinic's de-identified data set and to maintain an ongoing dialogue with clinicians to ensure proper understanding of data structure, patient population, and relevant clinical or health outcomes to be predicted.

In one embodiment of the invention, initial prediction model development work is performed as part of any of the following: (1) a collaborative agreement between company and clinic; (2) a consulting relationship in which the clinic consults the company; or (3) a data use agreement specific to the development of the prediction tool. Subsequent application of clinic-specific prediction models to relevant patients of the clinic may require a service agreement between the company and the clinic. It is to be understood that the present invention does not entail the sale or purchase of the de-identified data, rather, the present invention contemplates that the company is merely paying for the use of the de-identified data from the client solely for the use of product development. As previously noted, all agreements will necessarily be in compliance with HIPAA, HITECH, and privacy and consumer laws.

In another embodiment of the invention, individual users of the DSS platform of the present invention may be provided with an option to share their de-identified date under a data use agreement that will provide the individual with some form of compensation for the use of their de-identified data for the development of new prediction models and/or tools. Forms of compensation may vary. Individuals that agree to share their de-identified data sets will necessarily provide consent to the use of their de-identified data and may also be subject to an audit to ensure the accuracy of the provided personal health data. One example of a possible audit would be a request for a random selection of the individuals providing consent to provide copies of their medical files to the company. Any such audit would of course necessarily be in compliance with HIPAA, HITECH, and applicable privacy and consumer laws.

In a further embodiment of the invention, test output (typically in the form of a written or on-line report) shows the predicted probability of a certain outcome, and/or distribution of predicted probabilities vs. actual outcomes for the test population. For example, a test may be shown on a screen, such as a computer monitor, and the test may be saved as an image, emailed, or printed. Test output may be short (e.g., one page) or long (e.g., multiple pages to provide test result along with fully annotated educational materials).

In a further embodiment of the invention, the DSS comprises an application selected from the group consisting of an electronic application (eApp) that may be local (e.g., on a desktop or clinic server), an online web application, a mobile app, a web app designed for mobile devices, or an eApp that is integrated or connected with EHRs. The DSS applications of the present invention may comprise one or more of the following features:

a patient/consumer portal, a healthcare provider portal, and an enterprise portal (for administrative and technical support);

a display of information regarding each prediction model, any indications for use, and/or any prediction models that are available;

a data input form that is pre-formatted to request variables that are required to run each prediction model;

a database server that receives data that is entered on the data input form for archiving, transmission to computation server, and the retrieval of data during troubleshooting;

an analytics server to which the prediction models are integrated;

an output form that reports the test results (e.g., the probability of having a certain health outcome), a summary of any reference data, statistical specs of the prediction test, and any limitations and/or disclaimers;

a payment module; and web architecture and software to ensure secure access, and compliance with HIPAA, HITECH, and privacy and consumer laws.

It is to be understood that any DSS applications that are made by a company for a specific clinic (Clinic A) are applicable only to patients of that clinic without further development. In one embodiment of the invention, applications and accompanying clinic-specific DSS from a first clinic (Clinic A) may be applied to patients at a second clinic (Clinic B) if the following steps are performed:

a data use agreement is arranged between the company and Clinic B;

a validation test set is generated using the Clinic A prediction model with Clinic B's de-identified data sets and outcomes (i.e., a test set);

the test set shows new validation specs for Clinic B in the application and test output;

the Clinic B application and test output indicates Clinic A as the source of the original training; and Clinic A receives compensation for its data use in the form of a royalty that may be an annual flat fee or a percentage of any gross revenue generated directly from the sale of applications that use Clinic A's data.

In another embodiment of the invention, the DSS may include a Diversity Prediction Model to serve a wide range of clinics across a large geographic region. Under appropriate data use agreements arranged with each participating clinic, the data sets from each clinic may be pooled and merged to create a Diversity set, which is further divided into non-overlapping training and test sets. Since variables and structure of data sets may be similar (but not identical) and will typically be non-standard, the merging of data sets and the setting of inclusion and exclusion criteria will typically not be automated, but may require the collective expertise of a statistician, physician and scientist, to create and annotate the Diversity set.

In a further embodiment, the Diversity Prediction Models may include a second layer of validation against test sets obtained from other clinics that are not part of the Diversity set. In another embodiment, Diversity Prediction Models may be developed into two versions: one version for professional use by healthcare providers (e.g., for use in the "B to B" or "B to B to C" models, which are described below) and another version for direct use by the individual (e.g., for use in the "B to C" model, described below).

Methods, characteristics of the Diversity set, the independent test sets, and the validation results (e.g., the specifications of a product) may be disclosed on an application, such as for example an eApp, and summarized in the test output.

Clinics that license de-identified data towards the development of Diversity Prediction Models may be compensated by the company developing the Diversity Prediction Model. In one embodiment of the invention, a clinic may be compensated by the company with an annual flat fee or a percentage of the gross revenue generated from the use of Diversity Prediction Models. In another embodiment, a clinic may be compensated by the company based upon the relative size of the de-identified data set as a portion of the Diversity Set. In a further embodiment, a clinic may be compensated by the company according to the clinic's contribution to the establishment of phenotypic profiles obtained from the de-identified data sets. In another embodiment, a clinic may be compensated by the company according to the clinic's contribution to quantitative measures of the performance of the model, wherein the quantitative measures comprise predictive power, discrimination, calibration, and reclassification. In a further embodiment, the compensation scheme may be made transparent to all clinic contributors of the Diversity set.

The Diversity set may include without limitation, aggregate de-identified phenotypic data sets from clinics, phenotypic data sets with personal health identifiers (i.e., PHI-containing phenotypic data sets) from individuals, or a combination of aggregate and individual phenotypic data. The Diversity set may further comprise a library of de-identified phenotypic profiles, wherein the phenotypic profiling of an individual is carried out in real time against a library of known profiles for a particular health condition or disease state of interest. For example, an individual's profile, which may be submitted by an individual and/or the individual's healthcare provider, is matched in real time against a library of profiles by the Diversity Prediction Model, which determines the predicted outcome probabilities of a particular health condition or disease state based on outcomes of the most similar profiles in the library. Where an individual consents to the company's use of their data for the development of the Diversity Prediction Model, the individual may be compensated by a variety of mechanisms. In order to ensure data integrity, such individuals may be required to agree to an audit prior to the release of their data.

EHR Delivery Platforms

The present invention also includes methods of delivering EHRs that are focused on health and conditions related to a specific disease spectrum, such as but not limited to reproductive and fertility health, or other chronic health conditions by offering data input and output formats that are not usually available on an EMR or an EPHR targeted at general use. Examples of other chronic health conditions include without limitation, multiple sclerosis, rheumatoid arthritis, glaucoma, inflammatory bowel disease, transplant recipients, osteoporosis, and mental/neurologic function monitoring for patients at risk for Alzheimer's or Parkinson's)

The EHR platform of the present invention will typically have one or more of the following features:
- appropriate and clear language devoid of medical jargon to obtain data that is critical for effective use of decision support and consultation with healthcare provider(s);
- an output format that follows conventional formats used by healthcare providers and thereby enables efficient communications and consultation between the individual and any healthcare providers; and
- the option to authorize data-sharing access to healthcare providers via a healthcare provider portal.

The EHR of the present invention may also include premium-level services for an additional cost. Within the context of reproductive care and/or fertility treatments, premium-level services may include, without limitation, the option of phone assistance by an experienced fertility healthcare provider or counselor to assist in the completion of in EHR for the individual and/or the option of assistance by an experienced fertility counselor to assist in the completion of the EHR based on medical records submitted by the individual. Within the context of general disease states, premium-level services may include, without limitation, the option of a private, confidential medical consultation with a physician from a network of medical specialists in the disease area; the option of private, confidential counseling with a clinical psychologist and counselor from a network of psychologists in the disease area; and/or the option of a private chat and/or discussion with a scientist who is in the forefront of research in the disease area.

The EHR of the present invention may also include the option of having a medical interpreter to assist with any of the completion or implementation of any of the foregoing functions and/or features.

In another embodiment of the invention, the EHR may provide personalized health and medical educational content that is selected for the individual based on the data input that the individual has provided. Educational content may be in the form of short interactive feedback, such as "remember to take your daily folic acid" in response to data indicating that the individual is trying to conceive. Educational content may also be in the form of a short, medium or extended length article about a health condition or a slide show, short video (e.g., how to give yourself a subcutaneous injection of hormonal meds), or a webinar with specialists speaking on a certain topic.

The EHR of the present invention may be further tailored to provide social networking in the form of community blogs or the viewing of EHR profiles in aggregate without identifying factors. For example, the EHR may allow an individual to register to allow others to view their de-identified data regarding a specific condition or disease state viewed by others thus increasing the knowledge base regarding the particular condition or disease state. In one embodiment, the information in the aggregate EHR may be used in the development of a DSS of the present invention.

In a further embodiment, the EHR of the present invention may serve as a one-stop gateway to communicate any of the following: the ordering renewals of prescriptions from specialty pharmacies; the procurement of health products related to a disease area (e.g., books, home monitoring/testing kits, over-the-counter prescription); healthcare provider mapping, referrals, and appointments; and calendar functions, including alerts for medical appointments, lab tests, and medications.

The EHR platform of the present invention has the following advantages over non-electronic healthcare record platforms:
- the ability of patients to be intimately involved in their own healthcare;
- increased mobility of patients while decreasing redundancy of services (e.g., decreases the need to redo certain lab tests when consulting another physician); increase diagnostic accuracy and safety of medical management in the ER setting;
- improved follow up by healthcare providers;
- healthcare monitoring by family members or other caregivers;
- scalable and less expensive over time;
- efficient data collection for QA, development of new diagnostics, and decision support; and
- the ability to facilitate e-prescriptions and the accuracy of e-prescriptions.

Proper implementation and use of the EHR platforms of the present invention may have additional benefits, such as for example, employer and/or insurance incentives for healthy lifestyle changes; disease prediction tools; and/or disease management. As previously discussed, the EHR platforms may receive data from EMRs and may display lab results to show the individual's health status over time.

In an employment setting, use of the EHR of the present invention for health feedback may be paid for by insurance plans or employers; the premise being that healthier employees are more productive and have decreased use of healthcare resources. In use, an employee interacts with a web-based EHR as described herein to respond to questions regarding the employee's risk for heart disease and diabetes. If the answers to the questions regarding the employees risk of heart disease results in a determination (based upon a heart disease risk algorithm programmed into the EHR) that the employee is at risk for heart disease, the EHR provides the employee with information on how to reduce the risk, such as for example, reducing cholesterol through diet and/or medications, increased exercise, decrease in weight, cessation of smoking, etc. In a similar vein, if the answers to the questions regarding the employees risk of developing diabetes results in a determination (based upon a diabetes risk algorithm programmed into the EHR) that the employee is at risk for diabetes, the EHR provides the employee with information on how to reduce the risk, such as for example, changes to the employee's diet, recommended exercises, and suggested weigh ranges for optimal health.

In addition to providing health advice on lifestyle by improved food choices, exercise, and other activities, the EHR will also provide recommendations to the employee for products and/or resources that are specifically paid for either directly or indirectly via the employer supported health plan and the insurance carrier for the plan.

For disease prediction, the web-based EHR of the present invention may be focused on one or a few conditions and/or diseases or it may be more comprehensive and provide risk indicators for multiple diseases, e.g., the Biophysical 250. In another embodiment, the EHR may provide risk assessment of a panel of diseases with an optional module if the individual is interested in a specific disease. One example of the "few condition/disease alternative" is an EHR directed to prostate cancer and breast cancer. Another example is an EHR directed to pre-conceptional or prenatal assessment of potential genetic risks in progeny. Input will typically involve specific questions related to personal or family risk factors, the purchase of a lab test, and payment for lab test. The core business will preferably be the sale of a non-standard lab test that may not be readily available in standard clinical laboratories. The disease prediction HER may deliver test results directly to the individual, often with a counseling support service, or a physician authorized by the individual.

For disease management, a patient- or family-centric web-based EHR may be used to manage a chronic illness. Examples of chronic illnesses include without limitation, type II diabetes, multiple sclerosis, hypertension, rheumatoid arthritis, chronic renal disease. Preferably, the focus of the disease management EHR is on one or a few chronic illnesses that require frequent data input (e.g., home testing for blood glucose level, blood pressure readings, home urinalysis). Functions may include data storage, data viewing (e.g., in the form of charts, trends over time, etc.), transmission of lab results to physicians to minimize communication errors and time spent to collect data; immediate and/or periodic feedback (e.g., what dose of insulin to administer at a particular time, the adjustment dose for anti-hypertensive medications, follow-up physician appointments, appointment calendaring, etc.). Through use of the disease management EHR, physicians may be able to more efficiently monitor the progression of a disease in a patient and not have to rely on patient recall if symptoms are graded and inputted in real time.

It is to be understood that the EHR platforms described herein are all intended to require patient-level, non-institutional e-implementation of HIPAA and HITECH safeguards.

In one embodiment of the invention, the EHR system of the present invention is developed on an internet platform wherein an individual enters her fertility-focused health data from an internet browser into an EHR platform that is hosted by a secure HIPAA-compliant server. The personal fertility health data may be maintained for personal use only by the individual or it may be shared by the individual with their healthcare provider or insurance agency as desired. Upon recommendation by the individual's fertility healthcare provider, individuals may order fertility prediction testing via any available means for payment over the internet, such as for example, a credit card payment or an electronic funds transfer. In a preferred embodiment, the test results are delivered to patient-specified healthcare providers in the form of clinical decision support via software-as-a-service (SaaS).

In another embodiment, the present invention provides a "hybrid" EHR platform, which offers the individual a combination of clinic-oriented services and direct-to-consumer goods and services. To support this hybrid model, the EHR platform will meet at least the following three objectives: (1) it will capture the data that is required to run fertility treatment prognostic tests; (2) it will meet the complete spectrum of fertility EHR needs, which ranges from women who are trying to conceive to women who are actively undergoing infertility treatment; and (3) it will generate revenues from sources, such as the referral of high-quality fertility products, corporate sponsorships, and online pharmacy purchases. The hybrid EHR platform is expected to foster long-term relationships with the individuals as many individuals remain in the fertility-seeking realm for multiple years between the ages of 30 and 45. For example, an individual may initially use the EHR hybrid platform for fertility health record-keeping, and later, as the need arises, the individual may order personal fertility testing and related consumer products.

The fertility-focused EHR system of the present invention is targeted at the following individuals: (a) women who are trying to conceive; (b) women who have not been able to conceive naturally, and are seeing a primary care physician, an OB/GYN, or a specialist in Reproductive Endocrinology/Infertility (REI) to have a diagnostic workup; and (c) women who are undergoing infertility treatment with any of the following procedures: oral medication, surgery, hormonal stimulation of ovaries, artificial insemination, in vitro fertilization (IVF), and other modifications of standard IVF including, without limitation, intracytoplasmic sperm injection, IVF with donor eggs, use of donor embryos, donor sperm, and/or gestational carriers.

With both the internet and the hybrid EHR platforms, the fertility-focused EHR system of the present invention includes at least the following features: (A) questions and data entry fields phrased in a user-friendly manner with minimal use of medical terminology to enable data entry directly by the patient; and (B) the arrangement of the EHR data fields in electronic modules (e-modules). The following list is illustrative of the type of topics that can be incorporated into the EHR e-modules: pregnancy history; menstrual history (since onset of menstruation, and including details of current menstrual cycles); infertility diagnostics; infertility treatments, details, and outcomes; detailed ethnicity survey; family history; and general medical history.

In one embodiment of the invention, details on each topic in the e-module are obtained via user-friendly questionnaires that include pull-down menus, click answer boxes, or fill-in text boxes. Upon saving of data, data are re-presented to individuals in chart/grid/table formats for easy visualization. These formats are also similar to those used by physicians in conventional paper-charts, so that when/if the individual shares this EHR with her physician, the EHR will support efficient and accurate patient-physician communications. In a preferred embodiment, the data entry is longitudinal, which allows and encourages individuals and/or physicians to enter data as it becomes available. For example, historical data can be entered all at once while clinical data can also be entered upon receipt of test results.

In another embodiment of the invention, interactive features educate individuals and improve accuracy of data entry at the same time. For example, an individual can call up a pop-up box to see a brief explanation of why a certain question is being asked. For example, a pop-up box relating to the topic of height and weight may provide an explanation as follows: "Height and weight are needed to calculate Body Mass Index (BMI), which is an estimate of the amount of body fat. A very high BMI indicates excessive body fat, which may have a negative influence on treatment success, while a very low BMI indicates insufficient body fat, which may also have a negative impact on treatment success. It has been found that BMI affects fertility treatment outcomes to different extents for different patients; accordingly, the impact of BMI varies depending on other factors that affect outcomes."

The EHR system of the present invention allows individuals a great deal of flexibility in completing the EHR questionnaires. For example, individuals have the option of answering the questionnaire wherever desired, or to upload past clinical records (e.g., photocopies of physician notes, printouts of lab results, operative reports, etc.) as a portable document format (pdf) or a comparable format. The uploaded materials will be integrated into the EHR system in a searchable format in order to facilitate the extraction of meaningful data from the documents for outcomes analysis and predictions.

In another embodiment of the invention, the complete EHR data or partial data, in the forms of modules, can be provided in a printer-friendly version for printing to a printer or to a pdf. Patients are free to use or share downloaded pdf files, at their own risks. This EHR-independent way to share data provides patients with flexibility in data-sharing and does not burden EHR with excessive web logic requirements to provide multiple login features, which keeps the liability and costs down while maximizing security and protecting patients from unintentional data-sharing by patient. For example, an individual who has just downloaded the complete or partial EHR data can share the sensitive clinical data in the report with her male partner, by emailing or printing the downloadable pdf, without the EHR needing to provide access to the male partner. Similarly, if necessary, the individual has the option to share the sensitive information in the EHR report with her insurance company without obligating the EHR to provide access to insurance companies or other third parties. The complete inability of third parties to access the EHR data is important to reassure individuals that their data cannot not be shared unintentionally as a result of IT errors or sold to insurance companies for any purpose.

In a further embodiment of the invention, payment can be made by third-parties without data-sharing. For example, there may be situations in which insurance companies, employers, or other third parties, may wish to support the individuals' prognostic testing endeavors. With such third parties, the EHR system of the present invention will require the third parties to purchase promotional codes to be given to their individuals. Individuals can use the promotional codes instead of paying for the tests (e.g., by PAYPAL®, credit card, automated debit card deduction, or e-check). This arrangement allows third parties to support evidence-based decision-making by individuals without requiring individuals to share confidential clinical information, such as for example, symptoms, signs, treatment choice and outcome or, diagnostic and prognostic data. When individuals are informed about their personalized risks and benefits in pursuing a medical treatment, they will make decisions that lead to decreased risk of complications (e.g., multiple births).

In another embodiment, individuals can choose whether and how they would like to share data with their physicians. For example, the individual can specify the names of doctors, healthcare providers (e.g., IVF nurses), or third parties, such as insurance companies, with whom to share the EHR data. The individual also has the option to specify which modules are to be shared with each healthcare provider (e.g., the individual can request to share the module for a current treatment, but not the module on menstrual history, etc.). Further, the individual has the ability to specify the duration of data-sharing with the healthcare provider (e.g., one-time, request each time for one incident, share for 30 days, share for 60 days, etc., share until request to terminate sharing). In addition to the foregoing, the individual also has the option to specify whether a particular healthcare provider has viewing privileges or editing/data-entering privileges as well. This flexibility allows this EHR to function as a software-as-a-service (SaaS) based combination EMR/EPHR for clinics.

In a further embodiment of the invention, when an individual orders a test, she will be asked to approve of sharing the data with her physician for the purpose of data-verification.

In another embodiment of the invention, the EHR can serve as an EMR/EPHR with dual patient/healthcare provider data entry capabilities. A clinic or a physician may subscribe to the EHR at a low annual fee per patient. Such a clinic or "corporate" version may address the needs of a small to medium size clinics with minimal upfront cost. This corporate version will have additional features that allow a physician to view clinic summaries and statistics and it will also allow multiple users at the clinic to enter different types of data.

The EHR-Driven DSS

In one embodiment of the invention, individual clinics can host clinic-specific algorithms. For example, each doctor or doctors from the same clinic can ask for a clinic-specific algorithm to be generated. This clinic-specific algorithm would then be hosted exclusively for patients of that doctor and/or clinic. There are multiple ways in which clinics may request clinic-specific algorithms to be used. For example, the algorithms can be made exclusively available to patients of the clinic to provide a specific service. Alternatively, the algorithms can be made public to gain access and exposure to new patients. In this respect, it is to be understood that the clinic-specific algorithms may include, without limitation, algorithms directed to prognostics delivery methods or algorithms directed to marketing strategies for the clinics.

In another embodiment of the invention, some or all of the EHR-driven DSS can be provided at various pricing schemes, depending on the business model of the company. Examples of pricing schemes include, without limitation, any of the following: subscription on a monthly or annual basis; one-time membership; and complimentary access for one or all parts of the EHR-driven DSS.

In a further embodiment of the invention, the DSS test services can be paid for by the individual (e.g., through PAYPAL®, credit card, automated debit card deduction, or e-check); by the clinic and/or the doctor (e.g., by subscription; by the purchase of promotional codes, or by purchase by the clinic with the subsequent transfer of costs to the patient); or by a third party, such as employers, insurance companies or pharmaceutical companies (e.g., by the purchase of promotional codes to be given to the patient as determined by the third party). In one embodiment, complete sections of the EHR or specific tests ordered through the EHR can be sponsored by a third party, such as a pharmaceutical company, to be provided at no cost to the individual.

In another embodiment, interactive features of the EHR-driven DSS may include links to commercial products that specifically pertain to a particular topic on the page of the EHR. Alternatively, the commercial products may be located on a page that is dedicated to other commercial interests.

In a further embodiment, the EHR will include, or link to, a consultation platform that facilitates a private, virtual consultation with a physician on a one-to-one basis, at a pricing scheme that is transparent. For example, if an individual has a condition that is not sufficiently common to be represented in the algorithms (e.g., uterine septum) or an atypical or severe form of a common condition (e.g., stage IV endometriosis, unusually large fibroid, etc.), her personalized needs may be better met by consulting one or more experts who may not be located in the individual's geographical region. This consultation platform is distinct from doctors' blog sites, chat rooms, or TWITTER® (Twitter, Inc., San Francisco, Calif.). The consultation platform may include, without limitation, any of the following features and services: biographies of the participating physicians together with a secure method to contact them; physician schedules; a transparent payment method for obtaining the consultation, which is displayed upfront to avoid a negotiation process; a method for advance payment for the consultation by the individual; the holding of the fees in the platform during the course of the consultation; upon completion of the consultation, the forwarding of a percentage of the fees to the EHR for hosting the consultation; and the forwarding the remaining fees to the physician upon completion of the consultation.

Individuals may provide medical information to consulting physicians by sharing access to the EHR for a limited time. To make this feature of the most benefit to the consulting physicians, the individuals will have the ability to upload pdfs of old medical records to the EHR via a HIPAA-proofed, secure path. In order to implement this feature, non-negotiable consent forms, HIPAA disclosure forms, and consulting agreements are provided by the EHR-driven DSS platform.

It is to be understood that all PHIs entered into the EHRs for record keeping and/or to run the EHR-driven DSS are not intended for research and/or prediction use development, unless explicit consent is obtained by the individual prior to entering the PHIs into the EHR. Where consent from the individual is obtained, the present invention intends that any research or development work will comply with applicable legal and/or ethics review board requirements.

DSS and EHR-Driven DSS Computer and Business Architecture

The DSS of the present invention may be implemented by a business architecture system selected from the group consisting of: (a) business to business (B to B); (b) business to business to consumer (B to B to C); and (c) business to consumer (B to C).

With the B to B system, a clinic enters into a service agreement with a company whereby the company provides test services and charges the clinic a monthly subscription fee or charges the clinic on a per-test basis. In one embodiment, the costs for the tests may be on an escalating scale (e.g., the costs of the tests increases as more tests are ordered). Under the B to B system, all procedures are conducted on the clinic portal and the clinic is responsible for entering all clinical data. The clinic absorbs the cost of the test services as part of its overhead cost, because providing the decision support may improve quality of personalized counseling and care, promote transparency, attract patients, health plans, and make the clinic more competitive when negotiating reimbursement rates. In this regard, all clinic data and all billing procedures belong to the clinic. Upon its generation, the DSS test report is delivered to the healthcare provider only (either on-site at the clinic or remotely through an application); the healthcare provider then has responsibility to send or print a copy of the test report for the individual (i.e., the patient and/or consumer). The healthcare provider has the ability to authorize the test report to be viewable on the individual's portal; in this case, the test report may be delivered to the healthcare provider and the individual simultaneously. Lastly, marketing and sales efforts integrated into the B to B DSS are targeted only at the physicians and clinics because the individual has no responsibilities in the B to B system.

The B to B to C system is similar to the B to B system, but the cost of the test is directly charged to individual's on the patient portal, via a variety of payment mechanisms, such as but not limited to, PAYPAL® (PayPal, Inc., San Jose, Calif.), credit card, automated debit card deduction, or e-check. Alternatively, the individual or physician may charge the cost of the test to a third party (e.g., employer/sponsor, payer, health plan, federal health savings plan), or enter promotional codes provided by third party or another entity that is promoting the use of diagnostic code. In another embodiment, the healthcare provider pays the company for the test and then redirects the charges to the individual. It is to be understood that any charge passed to the individual will be carried out by the physician in a manner that ensures full compliance with state and federal health care laws. Participation by an individual in the process requires registration on the patient portal and agreement and acknowledgement of the company's privacy policy.

With the B to C system, all procedures are conducted on a consumer interface via the individual's login portal and the individuals (e.g., the e-health consumers) are responsible for the accuracy of the data entry and for direct payment of any services and/or goods that are purchased through the interface. Under this model, the individuals receive their test results directly. With this model, marketing and sales efforts are targeted at the individuals as consumers and because the individual is responsible for the data entry, each test is on a decelerating scale (e.g., the costs of the tests decrease as more tests are ordered).

Under the B to C system, the DSS may be a stand-alone tool or it may be integrated with an EHR. In the stand-alone version, an individual registers and agrees to the company's privacy policy (including any indications and limitations of the test) and then proceeds to enter date into the data input form, pay for the test, initiate the test (by for example selecting a menu option of "Run Test"), and receive the test result in the form of a secure link, a viewable page (e.g., an html page), or a downloadable/printable image (e.g., an PDF file). In one embodiment, the individual has the option to authorize sharing of input data and test report their healthcare provider. In the integrated version, the individual is able to access their information via a login portal to their EHR and select criteria from the EHR that is required in order to run the particular test.

FIG. 1 provides a schematic of an illustrative computing architecture for an EHR-driven DSS. As shown therein, three users who may be anyone selected from an individual, a healthcare provider, or an EHR administrator accesses the EHR platform of the present invention by way of a secure internet connection. The EHR-driven DSS is provided in the cloud computing environment and includes an HTTP server, a firewalled application server that communicates with analytic, database, and e-mail servers. Communication with the merchant account provider is necessarily secure and all servers in the cloud computing environment are backed-up to a dedicate back-up server. As shown in FIG. 1, a primary feature of the computing architecture of the claimed invention is a high level of security features to ensure the safety of the user information provided in the EHR-driven DS. It is to be understood that the computing architecture presented in FIG. 1 is merely one example of how to organize CPUs and servers to operate an EHR-driven DSS and that those skilled in the art may find alternative CPUs and servers to implement an EHR-driven DSS of the present invention.

It is to be understood that server and computing design of an EHR-driven DSS platform is scalable and highly secure and is in compliance with HIPAA, HITECH, and privacy and consumer laws. Security features include, without limitation, any of the following features: utilization of cloud computing by renting discrete remote servers; clinical data entered by patient/healthcare provider are stored in database server (DB) and are retrievable by algorithms, which reside in the application server (AP); encryption of database and user/functions/data log to facilitate third party auditing.

In one embodiment, backend development work may be performed on a server that retrieves and copies data from the DB, strips the data of PHIs, and stores the data on the server for development work. In this way, PHIs are not encountered on a day-to-day basis and the system is in full compliance with HIPAA, HITECH, and privacy and consumer laws.

The following discussion will describe how an EHR-driven DSS method of the present invention operates within a B to B system, wherein individuals being tested are the patients of physicians that are affiliated with a clinic. Clinical data entered by patients and/or healthcare providers is stored in a database server (DB) and is retrievable by algorithms, which reside in the application server (AP). Patient-specific algorithm results will populate pre-formatted output to produce test result, which are viewable and downloadable at the physician login. The physician who has been specified to receive the test results will receive an email notification that the test results are available to view. Within the context of fertility treatments, U.S. Ser. No. 12/496,493, filed on Jul. 1, 2009, describes how algorithms can be generated from a comprehensive data set and applied to analyze a large panel of clinical variables in an unbiased fashion, in order to predict, for example, the personalized likelihood of a live birth in IVF treatment.

After viewing the test results, the physician has the option to retrieve the test results via a downloadable pdf or to store the pdf in the EHR platform for viewing in the future (e.g., there is no requirement to download the pdf to the computer desktop or to print the pdf for the sole purpose of data archiving). In addition to the foregoing, if and when the physician thinks it is appropriate, the physician also has the option to release the test results to the patient. Once the test results have been released by the physical to the patient, the patient will receive an email notification that the test result is available for viewing, upon login to the EHR systems.

Utility of DSS, EHR, and EHR-Driven DSS Methods

As previously described, the DSS methods of the present invention may be used by individuals, healthcare providers, clinics, and hospitals to drive prediction models. Individuals typically seek prediction models by way of DSSs out of curiosity or in a desire to decrease the risk of an adverse outcome by modifying lifestyle habits, seeking medical intervention, or choosing one type of medical intervention over other options. Healthcare providers, clinics, and hospitals use DSS methods to develop predication models as tools to enable more effective healthcare. In addition to the foregoing traditional uses, the DSS methods of the present invention have additional utility for groups, such as professional health organizations or government agencies, to promote health awareness and drive public health campaigns.

Within the context of healthcare, a DSS according to the present invention may be developed for a given person, at a certain time point or under a certain health condition, by obtaining the following information: the patient population represented in the data set that is used to develop the algorithm and the characteristics of the patients in the data set; the size and structure of the data set; inclusion and exclusion criteria for the data set; the statistical method used to generate the algorithm; assumptions and limitations in applying the algorithm; the error range of predicted probabilities, and whether the algorithm and predictions have been validated in an independent population. Unlike prior DSS systems, many of which relied solely upon a link to a scientific paper as the source of the algorithm or an algorithm derived from aggregate data reported in a clinical paper, the DSS of the present invention uses precise selective criteria in order to develop the algorithm that is the basis of the DSS of the present invention.

An advantage of the DSS method of the present invention is that the data set used to determine the DSS prediction model takes into consideration criteria of patient populations, such as geographic location, socioeconomic factors, ethnicity, choice of health plans, and other factors that can influence the prediction outcome. By contrast, prior DSS systems typically rely solely upon the healthcare provider for decision support. Patients, healthcare organizations, and payors may expect a healthcare provider to consistently and accurately operate prognostic decision trees based on critical review of the literature and apply the correct judgment when translating that knowledge to support counseling of an individual patient. Because no two patients are the same, this system is not effective and places undue responsibility on the healthcare provider to act as a statistician and outcome predictor.

The DSS method of the present invention has utility in a variety of applications. In one embodiment, it allows for the biotechnology pipeline of prognostic biomarkers to be used beyond the original patient population. In other words, proper validation of biomarker with the DSS method of the present invention may result in the applicability of the biomarker in a patient population that is outside of the original patient pool. Such a system will allow patients outside of the original patient pool to have access to a biomarker that may not have been available to them under prior DSS systems.

Within the context of the EHR platforms of the present invention, as previously noted, even with individuals that keep highly accurate and organized health records, the self-invented format of the individuals is likely to be different from conventional formats used by healthcare providers. As a result, self-kept records may not enable optimal and efficient communications with healthcare providers, compromising both the individual's opportunity to seek optimal care and the opportunity of a competitive and qualified healthcare provider to grow and expand his/her practice. The EHR platform of the present invention overcomes this burden by providing an optimal platform for both the individual and the healthcare provider.

With EHR platform of the present invention also facilitates an individual's access to educational literature, community chat rooms, blogs, and e-procurement of pertinent health or lifestyle products. Prior to the present invention, an individual would have to shop and compare several sites to access each one of those tools and tolerate a tremendous amount of redundancy. The present invention streamlines the research process by tailoring products and services to a particular condition, such as fertility challenges, or the specific stage in a disease state.

Another advantage of the DSS and EHR methods of the present invention is the flexibility of the methods with regard to the use of the algorithms that are integral to the predication analyses previously discussed. While some physicians and/or clinics are interested in providing only customized, clinic-specific algorithms to their own patients, others are interested in making their customized algorithms available to other patients as co-developers. The EHR and DSS methods of the present invention allow the physicians and/or clinics to tailor algorithms to suit both of these needs. In this regards, within the context of the present invention, the use of algorithms on many patients without disclosing the actual algorithms or their structure is a feature of the SaaS-based platform previously discussed.

As previously described, the EHR-driven DSS of the present invention may be used to determine fertility outcomes of a female individual; however, the EHR-driven DSS is not exclusive to fertility outcomes and may be applied to other areas of medicine, and in different clinical settings. The following discussion illustrates these additional applications of the EHR-drive DSS method described herein.

Within the context of OB/GYN, women of adult age, who span the reproductive spectrum, can use the EHR-driven DSS method of the present invention to record clinical hormonal/reproductive data, such as for example, menstrual functions and contraceptive efforts, for the sole purpose of personal health record archiving or to screen for red flags that should alert women to see their physicians. Representation of clinical data in an intuitive medical format will support quick review of pertinent history by the physician and free up time to discuss health prevention and disease treatment during a consultation. For example, the EHR-driven DSS method of the present invention can be used to educate and clarify the healthcare provider's instructions to the patient with regard to the timing of contraceptive efforts.

In addition, the EHR-driven DSS method of the present invention may be used to detect menstrual/hormonal abnormalities and prompt women to address possible problems by seeing their physician. For example, a woman who enters her menstrual cycle dates into the EHR can request to be screened for potential abnormalities. If her menstrual pattern shows certain abnormal features, she will be alerted to see a physician, and will be prompted to answer additional questions. Common and possible problems, such as polycystic ovarian syndrome, for example, will be provided in the EHR database. Once a diagnosis is made by the patient's physician and entered into the EHR, the woman will be given specific educational materials that pertain to her condition, her age group, and other specifics relating to the patient's unique condition. This particular use of the EHR-driven DSS has particular utility for peri-menopausal women, many of who experience significant menstrual abnormalities that can last years. The EHR-driven DSS can track the patient's menstrual symptoms and/or any other health symptoms. Upon the identification of a problem, the EHR-driven DSS can provide notifications to the patient for doctor's visits and recommended medical tests. In addition to the foregoing, the EHR-driven DSS can also provide personalized education materials to the patient.

Within the context of other areas of medicine, the EHR-driven DSS can assimilate relevant clinical data to provide treatment-specific prognoses at one or multiple time points, for any of a wide range of cancers (e.g., breast, prostate, ovarian cancer). In a similar vein, the EHR-driven DSS can provide personalized prediction of treatment outcomes in a variety of out-patient disease states, such as for example, glaucoma, diabetes, heart disease, and chronic illnesses with potentially debilitating consequences, such as rheumatoid arthritis and multiple sclerosis. The EHR-driven DSS can also provide clinical decision-making assistance in inpatient applications and provide direct-to-consumer tests. Example of how the EHR-driven DSS can be applied in clinical decision making applications is with the optimization of intensive care unit protocols and with risk assessment analyses in order to select patients for protocols for the prevention of hospital-acquired infectious diseases. Example of how the EHR-driven DSS can be applied to direct-to-consumer applications is with procedures for the daily management of diabetes and/or diet and weight control.

In all scenarios, data may comprise demographics data (e.g., ethnicity, gender, socioeconomic, etc.); clinical data (e.g., symptoms, blood pressure, family history); laboratory tests, such as cholesterol profile, urinalysis, EKG findings; genetic test data; gene expression data (e.g., global or targeted gene expression analysis of a tumor sample); biomarkers such as protein, genomics, genetic data; textual data such as an operation report that can be subjected to textual search and conversion to values in data fields; images, such as ultrasound images of ovarian follicles that can be subjected to digital analysis and conversion to quantitative parameters, such as the number and size of ovarian follicles.

The present invention provides a way to overcome many of the challenges facing the clinics and physicians that serve patients as well as the patients themselves. Challenges facing clinics include, for example, insufficient personnel or resources to handle the administrative and billing procedures required of the clinics; insufficient resources to invest in infrastructural and workflow changes, and the reluctance of some clinics to take on the responsibility of payment collection. The present invention overcomes these challenges by providing a streamlined EHR platform that incorporates many of the administrative duties directly into the EHR-driven DSS platform, such as for example, requiring pre-payment for the ordered tests.

Challenges facing physicians include, for example, the resistant of some physicians to actively engage with computer- or internet-based tools and the continued desire on the part of some physicians to connect with patients in conventional consultation visits. The present invention overcomes these challenges by placing the data-entry requirements on the part of the patient, rather than the physician, and by delivering test results directly to the physician. In addition, the consultation feature of the EHR-driven DSS method allows the physician to actively consult with the patient.

Challenges facing patients include, for example, the varying ability of patients to perform internet-driven tasks, such as entering personal and clinical data into on-line forms and the desire of patients to receive consultation with their own physicians. The present invention overcomes these challenges by requiring patients to only enter their information one time into the EHR; thus, avoiding the need for the repeated entry of the same information for test-taking in the future. The consultation feature of the EHR-driven DSS method also allows patients to engage with their physician in a traditional one-on-one manner.

While the invention has been described in conjunction with the embodiments set forth above, the foregoing description is intended to illustrate and not limit the scope of the invention. Further, it is to be understood that the embodiments and examples set forth herein are not exhaustive and that modifications and variations of the invention will be apparent to those of ordinary skill in the art without departing from the scope and spirit of the invention.

All documents, including patent documents, cited herein are incorporated by reference in their entirety.

I claim:
1. A system comprising:
(a) an electronic health record (EHR) platform comprising a secure internet connection, wherein the EHR platform has questions and modules specific for at least one health condition or disease state, wherein a user pro- vides answers to the questions and enters information for a subject individual into the EHR platform by way of the secure internet connection, wherein the EHR platform is integrated with a decision support system (DSS), wherein the DSS comprises a prediction model for the at least one health condition or disease state;

(b) an application server (AP) comprising a customized algorithm developed with computer code comprising clinic-specific, region-specific, and/or population specific variables, wherein the AP is in communication with the EHR platform and the customized algorithm interprets information entered into the EHR platform to generate the prediction model for the at least one health condition or disease state;

(c) a database server (DP) that communicates with the AP, wherein the DB stores the information entered into the EHR platform and provides encryption to keep the information secure; and (d) a DSS test report showing a predicted probability of the at least one health condition or disease state for the subject individual, wherein the DSS test report comprises personalized predictions regarding treatment for the at least one health condition or disease state for the subject individual, wherein the personalized predictions are based upon the prediction model for the at least one health condition or disease state from the DSS and the information entered into the EHR platform by the user and the prediction model is validated with non-overlapping training and test sets against a set of quantitative and statistical criteria generated from the clinic-specific, region-specific, and/or population-specific variables, wherein the EHR platform comprises an interactive web portal to ordering renewals of prescriptions from specialty pharmacies; procurement of health products related to a disease area; healthcare provider referrals; healthcare provider appointments; and calendar alerts for medical appointments, lab tests, and medications.

2. The system of claim 1, wherein the user is selected from the group consisting of an individual, a physician, a healthcare provider, and a clinic administrator.

3. The system of claim 2, wherein the user may designate sharing privileges for the EHR platform.

4. The system of claim 3, wherein the sharing privileges may be tailored to specify time limits for sharing.

5. The system of claim 1, wherein the EHR platform is provided in an application selected from the group consisting of an electronic application on a local computer, an online web application, a mobile application, and a web-based application designed for mobile devices.

6. The system of claim 5, wherein the electronic application is located on a personal computer or a clinic server.

7. The system of claim 1, wherein the customized algorithm is developed using de-identified data from a single clinic.

8. The system of claim 1, wherein the customized algorithm is developed using de-identified data from more than one clinic.

9. The system of claim 1, wherein the clinic-specific, region-specific, and/or population-specific variables are selected from the group consisting of demographic variables, clinical variables, laboratory variables, or combinations thereof.

10. The system of claim 9, wherein the demographic variables are selected from the group consisting of ethnicity, household income level, and education.

11. The system of claim 9, wherein the laboratory variables are selected from the group consisting of test results of body fluids, tissue level data, imaging results, and biomarker test results.

12. The system of claim 11, wherein the tissue level data is selected from the group consisting of immunoassays, quantitative PCR (qPCR), semi-quantitative measurement of transcriptome by gene expression arrays, or whole-transcriptome sequencing.

13. The system of claim 9, wherein the biomarker test results are selected from the group consisting of genetic marker tests results and genetic data extracted from discovery platforms.

14. The system of claim 1, wherein the customized algorithm is developed using a statistical method selected from the group consisting of machine learning, logistic regression, linear regression, and combinations of any of the foregoing.

15. The system of claim 14, wherein the machine learning comprises a boosted tree approach.

16. The system of claim 1, wherein the quantitative and statistical criteria is selected from the group consisting of posterior probability of an event, area under the curve, calibration, and reclassification.

17. The system of claim 1, wherein the prediction model is a Diversity Prediction Model that includes a Diversity set selected from the group consisting of aggregate de-identified phenotypic data sets from clinics, phenotypic data sets with personal health identifiers from individuals, and a combination of aggregate and individual data sets.

18. The system of claim 17, wherein the Diversity Prediction Model comprises phenotypic profiles obtained from the de-identified data sets.

19. The system of claim 18, wherein phenotypic profiling for an individual is carried out in real-time against a library of known profiles.

20. The system of claim 17, wherein a clinic is compensated by a third party that is using the de-identified data sets for the development of the Diversity Prediction Model.

21. The system of claim 20, wherein a clinic is compensated by the third party based upon the relative size of the de-identified data set as a portion of the Diversity Set.

22. The system of claim 20, wherein a clinic is compensated by the third party according to the clinic's contribution to the establishment of phenotypic profiles obtained from the de-identified data sets.

23. The system of claim 20, wherein a clinic is compensated by the third party according to the clinic's contribution to quantitative measures of the performance of the model.

24. The system of claim 23, wherein the quantitative measures comprise predictive power, discrimination, calibration, and reclassification.

25. The system of claim 1, wherein the DSS is implemented in a business-to-business architecture, wherein the DSS is developed by a company and provided to a clinic without interaction by an individual.

26. The system of claim 1, wherein the DSS is implemented in a business-to-business-to-consumer architecture, wherein the DSS is developed by a company and provided to a clinic with interaction by an individual.

27. The system of claim 1, wherein the DSS is implemented in a business-to-consumer architecture, wherein the DSS is developed by a company and provided directly to an individual.

28. The system of claim 1, wherein the information entered into the EHR platform is personal health data of an individual.

29. The system of claim 1, wherein the EHR platform comprises support of clinic oriented services and direct to consumer goods and services.

30. The system of claim 1, wherein the EHR platform is specific for fertility treatments and the DSS provides personalized predictions of at least one fertility outcome for the individual.

31. The system of claim 30, wherein the at least one fertility outcome is the probability of a live birth event.

32. The system of claim 1, wherein the EHR platform is specific for menstrual and/or hormonal abnormalities and the DSS provides personalized predictions of possible conditions causing the menstrual and/or hormonal abnormalities in the individual.

33. The system of claim 1, wherein the at least one health condition or disease state is selected from the group consisting of cancer, glaucoma, diabetes, heart disease, rheumatoid arthritis, and multiple sclerosis.

34. The system of claim 1, wherein the EHR platform further comprises additional platforms selected from the group consisting of consultation platforms, consumer services platforms, and consumer goods platforms.

35. The system of claim 34, wherein the consultation platform comprises features selected from the group consisting of physician biographies, physician schedules, physician consultation request modules, and payment modules.

* * * * *